United States Patent [19]
Callejas et al.

[11] Patent Number: 5,463,159
[45] Date of Patent: Oct. 31, 1995

[54] THERMAL CRACKING PROCESS

[75] Inventors: Ricardo J. Callejas, Sweeny, Tex.; Gil J. Greenwood, Bartlesville, Okla.

[73] Assignee: Phillips Petroleum Company, Bartlesville, Okla.

[21] Appl. No.: 216,003

[22] Filed: Mar. 22, 1994

[51] Int. Cl.$^6$ .................................................. C07C 4/04
[52] U.S. Cl. ........................ 585/648; 585/650; 585/652; 208/48 R
[58] Field of Search ............................ 585/648, 649, 585/650, 651, 652; 208/48 R, 67

[56] References Cited

U.S. PATENT DOCUMENTS

| | | | |
|---|---|---|---|
| 4,206,036 | 6/1980 | Takeuchi et al. | 208/89 |
| 4,404,124 | 9/1983 | Johnson et al. | 252/466 |
| 4,658,081 | 4/1987 | Kolts | 585/651 |
| 5,015,358 | 5/1991 | Reed et al. | 208/48 AA |
| 5,120,892 | 6/1992 | Skraba | 585/652 |
| 5,169,515 | 12/1992 | Ngan et al. | 208/48 R |
| 5,190,634 | 3/1993 | Fernandez-Baujin et al. | 208/107 |
| 5,264,114 | 11/1993 | Dunbar | 208/48 HA |

*Primary Examiner*—Asok Pal
*Assistant Examiner*—Bekir L. Yildirim
*Attorney, Agent, or Firm*—Lucas K. Shay

[57] ABSTRACT

A thermal cracking process is provided which comprises contacting a thermal cracking furnace with a fluid stream which comprises steam, a hydrogen-containing fluid, and a hydrogen sulfide precursor such as dimethyl sulfide under a condition sufficient to effect the generation of hydrogen sulfide and thereafter introducing a steam fluid containing a saturated hydrocarbon under a condition sufficient to convert the saturated hydrocarbon to an olefinic compound.

20 Claims, No Drawings

THERMAL CRACKING PROCESS

FIELD OF THE INVENTION

The present invention relates to a process for thermal cracking of a fluid stream containing a hydrocarbon.

BACKGROUND OF THE INVENTION

In a process for producing an olefin compound, a fluid stream containing a saturated hydrocarbon such as ethane, propane, butane, pentane, naphtha, or mixtures of two or more thereof is fed into a thermal (or pyrolytic) cracking furnace. A diluent fluid such as steam is usually combined with the hydrocarbon feed material being introduced into the cracking furnace. Within the furnace, the saturated hydrocarbon is converted into an olefinic compound. For example, an ethane stream introduced into the cracking furnace is converted into ethylene and appreciable amounts of other hydrocarbons. A propane stream introduced into the furnace is converted to ethylene and propylene, and appreciable amounts of other hydrocarbons. Similarly, a mixture of saturated hydrocarbons containing ethane, propane, butane, pentane and naphtha is converted to a mixture of olefinic compounds containing ethylene, propylene, butenes, pentenes, and naphthalene. Olefinic compounds are an important class of industrial chemicals. For example, ethylene is a monomer or comonomer for making polyethylenes. Other uses of olefinic compounds are well known to those skilled in the art.

As a result of the thermal cracking of a hydrocarbon, the cracked product stream can also contain appreciable quantities of hydrogen, methane, acetylene, carbon monoxide, carbon dioxide, and pyrolytic products other than the olefinic compounds. At the furnace exit, the product stream is cooled to remove the heavier gases.

The carbon monoxide formed during the cracking of a hydrocarbon, if in excess quantity, can have a detrimental effect on downstream treatment process of the desired olefinic compound. For example, ethylene produced by thermal cracking of ethane generally is contaminated with small quantity of acetylene which is usually selectively hydrogenated to ethylene in a hydrogenation reactor. Carbon monoxide in excess quantity has been shown to significantly cool the temperature of the hydrogenation reactor thereby making the selective hydrogenation of acetylene considerably less effective.

During the thermal cracking process, a semi-pure carbon which is termed "coke" is also formed in the cracking furnace as a result of the furnace cracking operation. Coke is also formed in the heat exchangers used to cool the product stream flowing from the cracking furnace. In order to burn out the deposits of coke, a thermal cracking furnace is required to periodically shut down the furnace resulting in a substantial loss of production. Additionally, coke is a poor heat conductor. As coke is deposited, a higher furnace temperature is required to maintain the saturated hydrocarbon temperature in the cracking zone at a desired level resulting in increased fuel consumption and shorter furnace life.

Therefore, there is an ever-increasing need to improve the thermal cracking process by reducing the formation of carbon monoxide or coke, or both, during the cracking process. It would be a significant contribution to the art if an improved thermal cracking process were developed.

SUMMARY OF THE INVENTION

An object of the invention is to provide a thermal cracking process for pyrolysis of a saturated hydrocarbon. Another object of the invention is to provide a thermal cracking process having low concentration of carbon monoxide formation. A further object of the invention is to provide a thermal cracking process whereby a by-product fluid stream produced which contains hydrogen is reintroduced into the thermal cracking furnace during the start-up of the thermal cracking process. Other objects, features, and advantages will become more apparent as the invention is more fully disclosed hereinbelow.

According to a first embodiment of the present invention, a process for startup of a thermal cracking process for converting a saturated hydrocarbon into an olefinic compound is provided which comprises contacting a radiant tube (hereinafter referred to as a cracking tube) of a thermal cracking furnace with a fluid stream which comprises steam, a hydrogen-containing fluid, and a hydrogen sulfide precursor.

According to a second embodiment of the present invention, a thermal cracking process for converting a saturated hydrocarbon into an olefinic compound is provided which comprises contacting a cracking tube contained in a thermal cracking furnace with a fluid stream which comprises steam, a hydrogen-containing fluid, and a hydrogen sulfide precursor; and thereafter introducing a second fluid stream which comprises steam and a saturated hydrocarbon into the cracking tubes under conditions sufficiently effective to convert a saturated hydrocarbon into an olefinic compound.

DETAILED DESCRIPTION OF THE INVENTION

As used in the present invention, the term "fluid" denotes gas, liquid, or both. The term "saturated hydrocarbon" is referred to as any saturated hydrocarbon which can be convened to an olefinic compound by a thermal cracking process. An "olefinic compound" as used in this application is a hydrocarbon having at least one double bond between carbon atoms in the molecule. Generally, examples of saturated hydrocarbons include, but are not limited to, ethane, propane, butanes, pentane, naphtha, and combinations of two or more thereof. Examples of olefinic compounds include, but are not limited to, ethylene, propylene, butenes, pentenes, naphthalene, and combinations of two or more thereof.

According to the present invention, a cracking tube of a thermal cracking furnace is contacted with a fluid stream, which comprises steam, a hydrogen-containing fluid, and a hydrogen sulfide precursor under conditions sufficient to reduce the formation of carbon monoxide during a thermal cracking process, before a second fluid stream which comprises a hydrocarbon is introduced into the cracking tube of the cracking furnace for producing an olefinic compound.

The present invention process can be carried out in any suitable thermal cracking furnaces known in the art. Examples of such thermal cracking furnace are disclosed in U.S. Pat. Nos. 5,120,892, and 5,264,114, disclosures of which are incorporated herein by reference. Because cracking furnaces are well known to one skilled in the art and the choice of a suitable cracking furnace is generally a matter of preference to one skilled in the art, the description of a suitable thermal cracking furnace is omitted herein for the interest of brevity.

Generally, a fluid stream containing steam, a hydrogen-containing fluid, and a hydrogen sulfide precursor can be introduced into a thermal cracking furnace by any suitable means such as, for example, pressure. Because the means for introducing such fluid stream are well known to one skilled in the art, the description of which is omitted herein.

Steam is used in the invention as a diluent or carrier for the hydrogen-containing fluid, the hydrogen sulfide precursor, or the hydrocarbon stream. Steam can be generated by any heat exchange means. Steam can also be generated in-situ from liquid water by any known heat exchange means. Any quantity of steam can be used in the present invention as long as the quantity is effective in carrying the various fluids of the invention process. The fluid in the cracking tubes of a cracking furnace can be heated by any heat exchange means from about 1000° F. to about 2000° F.

The hydrogen-containing fluid can be a substantially pure hydrogen. It can also contain other gases such as, for example, nitrogen, methane, carbon dioxide, or mixtures thereof so long as the hydrogen-containing fluid contains at least about 2 mole %, preferably at least about 3 mole %, and most preferably at least 5 mole % of hydrogen. Because the exit fluid stream of the cracking furnace, after the desired olefinic product is recovered, also contains hydrogen within the range disclosed above, it is preferred that this exit fluid stream be recycled and reintroduced into the cracking furnace in the process of the invention. As used herein, unless otherwise indicated, the term "exit fluid" is referred to as a fluid stream which is part of the product stream and which does not include appreciable amounts of the desired olefinic compound products. Sometimes this exit fluid is referred to, in the thermal cracking industry, as tail gas which is also useful as fuel gas. The exit fluid generally comprises about 60 to about 80 mole % of hydrogen, about 20 to about 40 mole % of methane, and about 0.5 to about 3 mole % of ethylene.

Any hydrogen sulfide precursor which can generate hydrogen sulfide in a cracking tube of a cracking furnace at an elevated temperature, such as the temperature used in the thermal cracking process, can be used in the present invention. Examples of suitable hydrogen sulfide precursors include, but are not limited to, dimethyl sulfide, dimethyl disulfide, methyl mercaptan, ethyl mercaptan, propyl sulfides, butyl sulfides, and combinations of two or more thereof. The presently preferred hydrogen sulfide precursor is dimethyl sulfide because it is readily available and it is easy to use.

Wishing not to be bound by theory, it is believed that the hydrogen-containing fluid employed in the present invention facilitates the generation of hydrogen sulfide from a hydrogen sulfide precursor which is also used in the invention. Therefore, any quantity of hydrogen or hydrogen-containing fluid can be employed in the present invention as long as that quantity can effectively facilitate the generation of hydrogen sulfide from the hydrogen sulfide precursor. For example, the concentration of hydrogen can be in the range of from about 20 to about 1500 parts hydrogen per million of steam (ppm) by weight, preferably about 30 to about 1000 ppm, and most preferably 50 to 500 ppm.

Similarly, any quantity of hydrogen sulfide precursor can be employed in the present invention as long as that quantity can effectively be employed in a thermal cracking process for converting a saturated hydrocarbon to an olefinic compound. Generally, the concentration of the hydrogen sulfide precursor can be in the range of from about 20 to about 1500 parts of the hydrogen sulfide per million parts of steam (ppm) by weight, preferably about 30 to about 1000 ppm, and most preferably 50 to 500 ppm.

The time required for the contacting of the cracking tubes of the cracking furnace with the fluid stream can vary widely as long as an effective amount of hydrogen sulfide can be generated during the contacting for reducing the formation of carbon monoxide in a thermal cracking process. The time can be as short as about 5 seconds to as long as about 10 hours, preferably about 10 seconds to about 8 hours, most preferably from 20 seconds to 7 hours.

Although it is not necessary to preheat the cracking tube of the cracking furnace before the cracking tube is contacted with the fluid stream, it is preferred that the cracking tube be heated before contacting the cracking tube with the fluid stream for better cracking results. The furnace can be heated by any heat exchange means known in the art. The cracking furnace can be preheated to the temperature range described above, i.e., about 1000° F. to about 2000° F.

After the cracking tube(s) of the cracking furnace is contacted with a fluid stream which comprises steam, a hydrogen-containing fluid, and a hydrogen sulfide precursor, a second fluid stream comprising a saturated hydrocarbon and steam can be introduced into the cracking tube of the cracking furnace for converting the saturated hydrocarbon to an olefinic compound. The introduction of the second fluid stream can be carried out by the same means as those described above for introducing the first fluid stream to the cracking tubes of the cracking furnace. See also U.S. Pat. Nos. 5,120,892 and 5,264,114, disclosures of which are herein incorporated by reference.

Once the second fluid stream is introduced into the cracking tubes of the cracking furnace, the cracking reactions can take place at any suitable conditions that provide the necessary cracking to the desired olefinic compound product(s). Generally, the cracking temperature of the furnace can be in a range of from about 1000° F. to about 2000° F., preferably about 1000° F. to about 1800° F., and most preferably 1000° F. to 1700° F. A wide range of pressure can be applied to the cracking operation such as, for example, within a range of from about 1 psig to about 100 psig, preferably about 2 psig to about 75 psig, and most preferably 3 psig to 60 psig, at the outlet of the cracking tube of the cracking furnace. The time required for converting a saturated hydrocarbon to an olefinic compound can vary widely depending on the hydrocarbon used in the process, the olefinic compound(s) desired, and the rate of the introduction of the second fluid stream. Generally, the flow rate of the second fluid stream is in the range of from about 6,000 to about 20,000 pounds per hour per cracking coil (see Example II) depending on the capacity of the cracking furnace. The residence time of the hydrocarbon fluid, based on the rate described above, is generally in the range of from about 0.05 second to about 1 second.

The product stream of the cracking process generally is a fluid stream containing the desired olefinic products such as ethylene, propylene, butenes, and pentenes, and impurities including alkynes such as, for example, acetylene and acidic compounds such as hydrogen sulfide, carbon dioxide, and carbon monoxide. Other impurities such as olefins higher than 5 carbons and aromatic compounds can also be present in the product stream. Generally, these impurities can range from about 1 00 parts per million by weight (ppm) to about 4 weight %. These impurities must be removed so as to have a final end product which meets product specifications.

The product stream is generally first cooled by any heat exchange means to a temperature in the range of from about 30° C. to about 300° C. The cooled product stream is fed to a quench means wherein the cooled product stream can be, if desired, contacted with water or a quench solution having a sufficient concentration of, for example, an amine compound to remove some undesired impurities such as, for example, carbonyl compounds to produce a "quenched" product stream. The "quenched" product stream is then generally compressed by a suitable compression means such as a compressor to increase the pressure of the product stream. The product stream is subsequently transferred to a caustic washer wherein a caustic stream is introduced to further remove the acidic by-products such as hydrogen sulfide and carbon dioxide.

Thereafter, the product stream can be further introduced into a hydrogenation reactor whereby any alkynes are selectively hydrogenated to a desired olefinic compound. Thereafter, the concentration of any saturated hydrocarbons such as, for example, methane, ethane, propane, in the product stream can be significantly removed by a means such as demethanization, or deethanization, or depropanization to recover the desired olefinic compound(s). The remaining fluid stream containing hydrogen is defined as "exit fluid" or "tail gas" in the present invention. Because these processes and means are well known in the art, the description of which is omitted herein for the interest of brevity. See, for example, U.S. Pat. Nos. 4,404,124; 5,120,892, and 5,264,114.

The following examples are presented to further illustrate the present invention and are not intended to unduly limit the scope of the invention.

EXAMPLE I

This example illustrates a process for cracking ethane to ethylene without pretreating the cracking furnace by the process of the invention.

The cracking furnace used had 8 internal coils (1 coil =2 inlet cracking tubes which form 1 outlet tube) and had a total capacity of about 60,000 pounds per hour for ethane/propane mixture at 80 psig. The furnace was heated with fuel gas.

Steam was introduced into the cracking tubes at a rate of 6,000 pounds per coil per hour containing 300 ppm by weight of dimethyl sulfide while the furnace was being heated to 1250° F. The furnace was held at 1250° F. for 4–6 hours. Thereafter, the rate of steam was reduced to 2000 pounds per hour per coil. Ethane was steadily introduced into the steam stream, while the steam rate was reduced to 2000 pounds per hour per coil, to 7500 pounds per hour per coil in about 30 minutes. The furnace was heated upwardly to 1600° F. while ethane was being introduced. The process was then steadily run for about 40 days until it was necessary to shut down the operation to remove coke buildup in the coils.

The product stream of the ethane cracking process was cooled to 200° F. using water whereby steam was generated. At this point the carbon monoxide content was measured using an on-line gas chromatograph manufactured by Applied Automation, Inc., Bartlesville, Oklahoma. The initial carbon monoxide content in the product stream, measured by the analytical means in over 100 runs, was in the range of from 3000 ppm to 4000 ppm by weight. Because of the high initial CO content of the product stream, some batches of ethylene produced did not meet product specifications.

EXAMPLE II

This example demonstrates the reduction of carbon monoxide content in an ethane cracking process using the process of the invention.

The runs were carried out the same as those described in Example I with the exception that, before ethane was introduced into the cracking tubes, the cracking tubes were contacted with a fluid stream containing steam, dimethyl sulfide, and a hydrogen-containing gas. In these runs, a tail gas containing from about 11 to about 26 mole % hydrogen, about 60 to about 77 mole % methane, about 1 to about 3 mole % $CO_2$, about 1 to about 3 mole % nitrogen, about 0.5 to about 3 mole % ethylene, and sometimes trace amount of acetylene was used as a hydrogen containing gas and was pressurized at a rate of about 28.4 standard $ft^3$/min. into the steam stream.

The initial carbon monoxide content of the invention runs were in the range of from about 380 to about 1180 ppm by weight for more than 24 runs. These results clearly demonstrate that using the present invention, the CO content in the cracking process was reduced by as much as 90%, a significant improvement over the results shown in Example I. Reduction in fluctuation of CO content facilitates the selective hydrogenation of acetylene to ethylene to produce products meeting product specification.

The results shown in the above examples clearly demonstrate that the present invention is well adapted to carry out the objects and attain the end and advantages mentioned as well as those inherent therein. While modifications may be made by those skilled in the art, such modifications are encompassed within the spirit of the present invention as defined by the specification and the claims.

That which is claimed:

1. A process comprising contacting a cracking tube of a thermal cracking furnace, used in a thermal cracking process for converting a saturated hydrocarbon to an olefinic compound, with a fluid stream which consists essentially of steam, a hydrogen-containing fluid, and a hydrogen sulfide precursor under conditions sufficient to effect the generation of hydrogen sulfide in said cracking tube before a saturated hydrocarbon is introduced into said cracking tube.

2. A process according to claim 1 wherein said hydrogen-containing fluid is an exit fluid or tail gas produced in said thermal cracking process.

3. A process according to claim 1 wherein said hydrogen sulfide precursor is dimethyl sulfide.

4. A process according to claim 1 wherein said saturated hydrocarbon is selected from ethane, propane, butane, pentane, naphtha, and combinations of two or more thereof.

5. A process according to claim 1 wherein said saturated hydrocarbon is ethane.

6. A process according to claim 1 wherein said saturated hydrocarbon is propane.

7. A process according to claim 1 wherein said hydrogen-containing fluid further comprises methane and ethylene.

8. A process according to claim 7 wherein the concentration of hydrogen of the hydrogen-containing fluid is present in said fluid stream is in the range of from about 20 to about 1500 parts per million by weight (ppm).

9. A process according to claim 8 wherein said range is from 50 to 500 parts per million by weight.

10. A process for reducing the formation of carbon monoxide or coke during a thermal cracking process comprising: (1) contacting a thermal cracking tube, which is used in said thermal cracking process for converting a saturated hydrocarbon to an olefinic compound, with a fluid stream which consists essentially of steam, a hydrogen-containing fluid, and a hydrogen sulfide precursor under a condition sufficient to effect the generation of hydrogen sulfide in said cracking furnace; and thereafter (2) introducing a second fluid stream which comprises a saturated hydrocarbon into said thermal cracking furnace under a condition sufficient to effect the conversion of said saturated hydrocarbon to a product stream which comprises an olefinic compound.

11. A process according to claim 10 wherein said hydrogen-containing fluid is an exit fluid or tail gas produced in said thermal cracking process.

12. A process according to claim 10 wherein said hydrogen sulfide precursor is dimethyl sulfide.

13. A process according to claim 10 wherein said saturated hydrocarbon is selected from ethane, propane, butane, pentane, naphtha, and combinations of two or more thereof.

14. A process according to claim 10 wherein said saturated hydrocarbon is ethane.

15. A process according to claim 10 wherein said saturated hydrocarbon is propane.

16. A process according to claim 10 wherein said hydrogen-containing fluid further comprises methane and ethylene.

17. A process according to claim 10 wherein the concentration of hydrogen of said hydrogen-containing fluid is present in said second fluid in the range of from about 20 to about 1500 parts per million by weight.

18. A process according to claim 17 wherein said range is from 50 to 500 parts per million by weight.

19. A thermal cracking process for converting ethane to ethylene comprising: (1) contacting a cracking tube with a fluid stream which consists essentially of steam, an exit fluid or tail gas of said thermal cracking process, and dimethyl sulfide at a temperature in the range of from about 1000° F. to 2000 ° F. and under a pressure in the range of from about 1 psig to about 100 psig; and thereafter (2) introducing a second fluid which comprises steam and ethane into said cracking tube.

20. A process according to claim 19 wherein said exit fluid or tail gas contains 50 to 1500 parts per million by weight of hydrogen.

* * * * *